United States Patent [19]

De Crosta et al.

[11] Patent Number: 5,252,729
[45] Date of Patent: Oct. 12, 1993

[54] EXTRACTION OF COMPOUNDS FROM PLANT MATERIALS USING SUPERCRITICAL FLUIDS

[75] Inventors: Michelle A. De Crosta, Bethlehem, Pa.; Peter Kabasakalian, Bloomfield; Frederick J. F. Honold, Sr., Fanwood, both of N.J.

[73] Assignee: Schering Corporation, Kenilworth, N.J.

[21] Appl. No.: 781,469

[22] Filed: Oct. 23, 1991

[51] Int. Cl.$^5$ .................. C07J 75/00; C07J 9/00; C07J 21/00; C07C 51/09
[52] U.S. Cl. .................................. 540/18; 540/17; 552/530; 552/540; 552/545; 552/549; 552/617; 552/618; 536/6.3; 554/11
[58] Field of Search .................. 540/18, 17; 552/545, 552/549, 617, 530, 540, 618; 260/415, 416, 424; 554/11; 536/6.3

[56] References Cited

PUBLICATIONS

Bonnie A. Charpentier and Michael R. Sevenants (eds.), Supercritical Fluid Extraction and Chromatography, Techniques and Application, Chapter 7, ACS Symposium Series 366, American Chemical Society, Washington, D.C. (1988), pp. 127-143.
Bioprocessing Technology, monthly intelligence service from Technical Insights, Inc., vol. 11, Nov. 1988, one page.
J. M. Wong and K. P. Johnston, Biotechnology Progress, vol. 2, No. 1 Mar. 1986, pp. 29-39.
CA111(17):152345q Imanishi et al., 1989.
CA110(19):171960g Brunetti et al, 1989.
CA109(16):135032b Eatherton, et al. 1988.
CA109(9):72333c Choi, et al. 1988.
CA109(4):24507r Kubota et al. 1989.
CA108(9):73925p Eisenbach et al., 1987.
CA108(7):52449w Kamarei, et al, 1987.
CA104(25):223476b Wong, et al. 1986.
CA102(9):79194x Stahl, et al. 1984.
CA97(16):134281d Chrastil et al, 1982.
CA112(7):53970d Bradley, 1989.
CA111(19):172661t Kankare et al, 1989.
CA110(7):56213d Hardardottir, 1988.
CA109(17):147995f Randolph et al, 1988.
CA109(10):75630h Kubota et al, 1988.
CA109(1):2942b Randolph et al, 1988.
CA108(17):146078b Randolph et al, 1988.
CA107(15):133045t Fujimoto et al, 1987.
CA105(3):23291w Shishikura et al, 1986.
CA111(22):195652e Yamamoto et al, 1989.
CA110(22):195390x Tavana et al, 1989.
CA108(7):52449w Kamarei et al, 1987.
CA104(4):24980m Schmitt, 1985.
CA71(22):103637h Pradhan, 1969.
CA113(2):7155q Ryan, et al, 1990.
CA112(18):171483v Hawthorne et al, 1990.
CA112(18):171431b Levy et al, 1989.
CA112(8):57164s Schmidt et al, 1989.
CA109(18):152169u Wright et al, 1987.
CA105(10):90485a Hawthorne et al., 1986.
CA99(16):129082b Proccacia et al., 1983.
G. Lopez Sanchez, et al., Analyst, Dec. 1972, vol. 97, pp. 973-976.
Price quote dated May 8, 1992 and picture of "Dense Gas Management System" for Supercritical Fluid Extraction (2 pages).
Page 1621 of 1992 from catalog of Aldrich Chemical Company, Inc. for "Soxhlet extraction apparatus".
Taber's Cyclopedic Medical Dictionary p. 1628, Nov. 1987.
Lopez, et al. Chemical Abs. vol. 78, 1973 Abstract 81734c.
Sharma, et al., J. Agric. Food Chem. 1991 39 508-510.
Fasman, CRC Handbook of Biochemistry and Molecular Biology, 3rd Edition, Lipids Carboyhydrates Steroids (1987, CRC Press, Cleveland, Ohio) pp. 544-549.

*Primary Examiner*—Mukund J. Shah
*Assistant Examiner*—E. C. Ward
*Attorney, Agent, or Firm*—Joseph T. Majka; James M. Gould; Eric S. Dicker

[57] ABSTRACT

The present invention is directed toward a process for extracting compounds from plant material, comprising
  a) contacting hydrolyzed plant material with a supercritical fluid and optionally with a co-solvent and
  b) recovering the compound from the supercritical fluid.

In another embodiment, the present invention is directed toward a process for removing a compound from plant material, comprising contacting the plant material with an acid, a supercritical fluid and a co-solvent, and recovering the compound from the supercritical fluid. The sterols, diosgenin and sarsapogenin, are efficiently extracted from barbasco root and Yucca seed, respectively.

19 Claims, No Drawings

5,252,729

EXTRACTION OF COMPOUNDS FROM PLANT MATERIALS USING SUPERCRITICAL FLUIDS

BACKGROUND

Processes for extracting numerous compounds from organic materials, particularly from plants, using supercritical fluid extraction (SFE) are known. Generally, above a critical temperature ($T_c$) and pressure ($P_c$), a vapor and a liquid of the same substance have the same density; in this state the fluid cannot be liquified by further increasing the pressure. A supercritical fluid state results when the substance is maintained at its $T_c$ and $P_c$ whereby a transition from gas/liquid to supercritical liquid occurs. For example, a description of the phase changes in a gas ($CO_2$) and the conditions at which the gas becomes a supercritical fluid (SCF) is known, as described in U.S. Pat. No. 4,749,522.

U.S. Pat. No. 3,899,398 to Cole et al. teaches a process for treating citrus wastes to obtain essential oils by cooking the citrus wastes in the aqueous phase under autogeneous pressure at a temperature of about 350° C. to 750° C., in the absence of air or oxygen.

U.S. Pat. No. 4,749,522 to Kamarei discloses supercritical fluid extraction of animal derived materials and provides generalized teachings that numerous methods can be used to prepared non-dried animal tissues used in the supercritical extraction process, including grinding, crushing, cumminuting, high and low pressure pressing, cryogrinding, flaking, sonication, freezing, freeze-thaw treatment, freeze drying, emulsification, homogenization, filtration, high speed mixing, centrifugation, cell separation, mechanical separation, thermal treatment, and other physical treatment such as treatment with inorganic and organic acids, bases, solvents, surface active agents, colorants, ionization radiation treatment; enzymatic treatment such as endogenous and/or exogenous enzymatic treatment, and any combination of more than one of the above methods of treating the sample. However, in none of his examples does Kamarei teach using treatment with acids of any kind. Nor does Kamarei suggest the use of his process for treating plant materials.

U.S. Pat. No. 4,824,570 discloses a process for supercritical extraction of essential oils from plants with carbon dioxide for preparing pharmaceutical products.

Bonnie A. Charpentier and Michael R. Sevenants (eds.), Supercritical Fluid Extraction and Chromatography, Techniques and Applications, ACS Symposium Series 366, American Chemical Society, Washington, D.C. (1988) discloses, for example, the ultrasonic supercritical fluid extraction (sfe) of caffeine from roasted coffee beans, of omega-3 fatty acids from fish oil and of terpenes from orange essential oil. Carpentier and Sevenants also discloses in Chapter 7, steps to developing a commercial supercritical carbon dioxide processing plant, and teaches that most solvent extraction using $CO_2$ are run at temperatures between 10° C. and 50° C., mild temperatures which are not likely to degrade or volatize heat-sensitive aroma compounds. The authors further teach that some materials may require pre-treatment processing (i.e. physical methods) to prepare the material for extraction or post-treatment of the residue after extraction is completed, further stating that materials handling systems such as conveyors and product silos must be designed with these considerations in mind.

Bioprocessing Technology, a monthly intelligence service from Technical Insights, Inc., Vol. 11, Number 11, November 1988 discloses that supercritical fluids, using as its solvent carbon dioxide, can be used to isolate diosgenin, a building block for sterols from plant cell culture.

J. M. Wong and K. P. Johnston, Biotechnology Progress, Vol. 2, No. 1, March 1986, pp. 29-39 teach the solubilization of biomolecules, such as sterols, in carbon dioxide based supercritical fluids.

L. Sanchez et al., Analyst (London) 97 (1161) pp. 973-6 (Chem. Abstract 78(13):81734c) teach that crude diosgenin was obtained from barbasco root by hydrolysis with 30% HCl followed by extraction with $CHCl_3$.

None of these references teach supercritical fluid extraction of compounds from plant materials which were hydrolyzed either prior to or during contacting with a supercritical fluid.

SUMMARY OF THE INVENTION

The present invention is directed toward a process for extracting a compound from plant material, comprising
 a) contacting hydrolyzed plant material with a supercritical fluid, optionally with a co-solvent, and
 b) recovering the compound from the supercritical fluid.

In another embodiment, the present invention is directed toward a process for removing a compound from plant material, comprising contacting the plant material with an acid, a supercritical fluid and a co-solvent, and recovering the compound from the supercritical fluid.

One advantage of the present invention is that it provides a process for extracting compounds having pharmaceutical utility from plant material in excellent yields and of high purity.

A second advantage of the present process is that it can utilize either fresh or dried plant materials, thus making the process extremely versatile in conjunction with off-site harvesting practices.

A third advantage of the present process it that it can utilize coarsely ground plant material, thus simplifying physical pretreatment operations, such as grinding and sieving.

A fourth advantage is that the present process generates considerably less waste, i.e. solvents, requiring much less handling and disposal than other known processes for extracting compounds from plant material.

A fifth advantage is that the present process is easily amenable to automation procedures and online analysis of the compounds being extracted from said plant materials.

DETAILED DESCRIPTION OF THE INVENTION

Throughout the specification, the terms "removal" and "extraction" have the same meaning and are used interchangeably.

An apparatus for supercritical extraction is made up of a extraction cell, preferably cylindrical, which is housed in a chamber for controlling temperatures and pressures. A supercritical fluid (ie. extracting mobile phase), such as $CO_2$, is pumped into the extraction cell, through a pressure regulating restrictor and into a vessel which serves as a trap. Pressure is maintained by back pressure regulators. As the supercritical fluid passes through the plant material containing the desired compound, the supercritical fluid removes the compound from the plant material. As the supercritical fluid containing the desired compound leaves the chamber, the fluid transforms into a gas, which passes through or is injected into (i.e. bubbling) a trapping vessel. The desired compound extracted from the plant material is concentrated in the trapping vessel.

The plant material can include the entire plant itself or any part thereof, including the roots, stems, leaves, fruits, flowers, seeds, tubers and the like, such as Barbasco root and Yucca seed.

Generally, the compound being extracted from the plant material should be resistant to hydrolysis by acid, although a compound which is oxidized or derivatized compounds can also be extracted. A compound is considered resistant to hydrolysis if the compound is not degraded by acid hydrolysis, even though certain acid labile moieties, e.g. esters, aldehydes, ketones, ethers, unsaturated double and triple bonds, etc. may undergo reaction with the acid and/or solvent. Where an oxidized or derivatized compound is extracted, the compound can be used as is, or can be converted to its original form by conventional procedures, e.g. reduction, esterification, addition, etc. as described in J. March, Advanced Organic Chemistry, 3rd Edition, John Wiley and Sons, New York, N.Y., (1985), 1346 pages.

Thus, the present process is useful for extracting from plant materials sterol compounds such as diosgenin, sarsasapogenin or cholestorol, and fatty acids such as C-8 to C-24 fatty acids, including octanoic acid, hexadecanoic acid, tetradecanoic acid and the like.

In the present process, hydrolyzed plant material can be prepared by treatment of fresh or dried plant material with acid under conditions effective to promote hydrolysis. Although partially hydrolyzed plant material can used in the present process, it is preferred that the plant material is completely hydrolyzed to maximize yields of the desired compound from the plant material. Useful acids for hydrolyzing the plant material can include mineral acids such as sulfuric acid ($H_2SO_4$), hydrochloric acid (HCl) or phosphoric acid ($H_3PO_4$); or organic acids such as formic acid, acetic acid, propanoic acid, butyric acid, o-, m- or p-toluene sulfonic acid, benzoic acid, trichloroacetic acid, trifluoroacetic acid; or mixtures of any of the above acids.

The acid can be employed in amounts sufficient to at least partially hydrolyze the plant material either prior to or during treatment with the supercritical fluid. Such amounts can range from excess to about equimolar amounts of acid per mole of compound anticipated to be removed or extracted from the plant material, preferably from about 100 to about 10 moles acid per mole of compound being extracted, more preferably from about 75 to about 25 moles of acid, most preferably about 50 moles acid. For example, if it is anticipated a barbasco root contains about 5% diosgenin, a treatment of about 50 moles acid per mole of diosgenin would utilize about one gram of acid per 0.5 gram of root material to completely hydrolyze the root material.

The acid solution should be thoroughly mixed with the plant material to allow maximum contact and penetration by the acid, by employing methods such as shaking, stirring, vortexing or sonicating the acid and plant material.

The plant material can be hydrolyzed with the acid at temperatures and pressures effective to promote hydrolysis of the plant material. Such temperatures can range from about ambient to about the boiling point of the acid solution, such as from about 25° C. to about 300° C., more preferably about 110° C. The pressures can range from ambient to the elevated pressures associated with the increased temperatures of the acid in the reactor.

Optionally, base can be added during or at the completion of hydrolysis of the root to neutralize any excess acid. Suitable bases include hydroxides, carbonates and bicarbonates of an alkali metal such as sodium, lithium, potassium or of an alkaline earth metal such as calcium or magnesium. Preferably the base is lime or sodium hydroxide, due their lower costs and availability. The base can be employed in amounts ranging from excess to about equimolar amounts of acid associated with the root and/or reaction mixture.

The supercritical fluid employed in the present process can be any of those described in U.S. Pat. No. 4,749,522. Representative extracting (solvating) mobile phase components include the elemental gases such as helium, argon, nitrogen and the like; inorganic compounds such as ammonia, carbon dioxide, water, and the like; organic compounds such as C-1 to C-5 alkanes or alkyl halides such as monofluoro methane, butane, propane carbon tetrachloride, and the like; or combinations of any of the above. A supercritical fluid can be modified by the addition of inorganic and/or organic compounds as listed above, called modifiers. Most preferably, the supercritical fluid is carbon dioxide admixed with chloroform. Not all the fluids described above will be suitable for extracting a desired compound from plant material. However, by determining the known properties of the desired compound as well as the gas specifications, including supercritical temperatures and pressures, one of ordinary skill in the art can select those components or any combinations thereof suitable for the extraction process.

The cosolvent employed in the present process should be compatible with the supercritical fluid selected and also be capable of at least partially dissolving the compound being extracted. Suitable co-solvents for use in conjunction with the supercritical fluid include aromatics such as xylene, toluene and benzene; aliphatics such as C-5 to C-20 alkanes including hexane, heptane and octane; water; C-1 to C-10 alcohols such as methanol, ethanol, propanol, butanol and isopropanol; ethers; acetone; chlorinated hydrocarbons such as chloroform, carbon tetrachloride or methylene chloride; or mixtures of any of the above. The co-solvent can be employed in amounts effective to aid in the wetting and/or hydrolysis of the plant material, and can range from excess to about one volume of solvent per one volume of acid, preferably from about 10 to one volume of solvent per one volume of acid. Where non-hydrolyzed plant material is used, a solvent should be used. However, where hydrolyzed plant material is used, the process can be conducted optionally with a solvent such as any of those described above; or the process using hydrolyzed plant materials (e.g. pre-hydrolyzed plant materials) can be conducted without a solvent. Preferably the process using hydrolyzed materials does not use a solvent.

The plant material can be contacted with the supercritical fluid at temperatures ranging from about 30° C. to about 300° C., preferably from about 75° C. to about 250° C. The pressure employed should be sufficient to maintain the supercritical fluid, and can be increased from ambient atmospheric pressure to about 400 atmospheres or more, preferably between about 100 and 300 atmospheres. Preferably the apparatus is programmed to maintain slow, incremental increases in pressure to achieve efficient extraction of the compound from the plant material and avoid abrupt sample movements or plugging of the output lines.

The compound being extracted can be recovered from the supercritical fluid by passing through or injecting the mobile phase into a trapping solvent within which the desired compound is readily soluble, such as any of the solvents described above for use with the supercritical fluid. The compound can be recovered from the trapping solvent using conventional recovery procedures such as evaporation, distillation, phase separation, or crystallization or filtration.

EXAMPLE 1

Extraction of Diosgenin from Fresh Barbasco Root Hydrolyzed During Supercritical Fluid Extraction

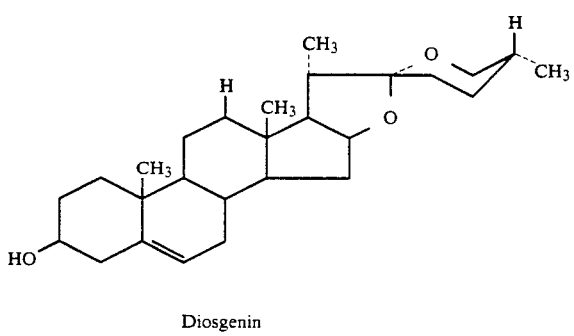

Diosgenin

To a ten mL stainless steel extraction cell is added 0.5 g dried, coarsely ground barbasco root, 2 mL of isopropyl alcohol and 2 mL of 3N para-toluene sulfonic acid (PTSA). The extraction cell is sonicated for 15 minutes to mix the contents of the extraction cell. The extraction cell is opened and about one inch of prewashed sand is added and packed at the fritted restrictor end of the cell (i.e. output). The extraction cell is closed and inserted into a supercritical extraction unit with the sand filled end attached to the restrictor. The input is attached to the opposite end. The operating conditions are as follows:

| | |
|---|---|
| Head Space Filler: | Helium |
| Restrictor Flow: | 500 mL/min |
| Extracting Mobile Phase (i.e. supercritical fluid): | Supercritical fluid grade $CO_2$ modified with 10% chloroform |
| Oven Temperature: | 250° C. |
| Trapping Solvent: | Toluene |
| Pressure Program: | a. 100 atm. for 2 minutes |
| | b. 200 atm. for 2 minutes |
| | c. 225 atm. for 2 minutes |
| | d. 250 atm. for 2 minutes |
| | e. 275 atm. for 2 minutes |
| | f. 300 atm. for 60 minutes |
| Total Extraction Time: | 70 minutes |

Analysis of the trapping solvent containing the extracted compound by supercritical fluid chromatography (SFC) and comparison with known standards indicates that 100+10% of the diosgenin from the barbasco root, depending upon sample homogeneity, is extracted.

EXAMPLE 2

Extraction of Diosgenin From Dry Barbasco Root Which is Acid Hydrolyzed Prior to Supercritical Fluid Extraction a. Hydrolysis of root. To a five liter glass lined, three-necked reactor equipped with an overhead stirrer, thermometer, condenser, addition funnel and agitator, is added 1860 ml tap water and 282 g sulfuric acid. Under agitation, the flask is charged with 1000 g of air dried barbasco roots (equivalent to about 40 g diosgenin). The reactor is closed and heated with steam to a temperature of 110° C. for two hours, during which time 592 ml water is added. The reaction mixture is cooled to 90° C., the reactor is vented to allow the air space within the reactor to equilibrate to atmospheric pressure, and the reactor is charged with 1200 mL of hot water. The acidified water is drained from the roots. The roots are washed with additional hot water, flushed with steam for 30 minutes and dried at 80° C. overnight to give hydrolyzed roots.

b. Supercritical fluid extraction. Essentially the same procedure as in Example 1 is employed, except that sonication is eliminated and only hydrolyzed barbasco root from step a. and prewashed sand are added to the extraction cell. Analysis of the trapping solvent indicates that 100±10% of the diosgenin from the barbasco root is extracted.

We claim:
1. A process for extracting a compound from plant material, comprising
 a) contacting acid-hydrolyzed plant material with a supercritical fluid, optionally with a co-solvent, and
 b) recovering the compound from the supercritical fluid.
2. The process of claim 1 wherein the compound being extracted is a sterol compound or a fatty acid.
3. The process of claim 1 wherein the plant material is hydrolyzed with a mineral or organic acid.
4. The process of claim 3 wherein the mineral acid is sulfuric or hydrochloric acid.
5. The process of claim 3 wherein the organic acid is paratoluene sulfonic acid.
6. The process of claim 1 wherein the supercritical fluid is carbon dioxide.
7. The process of claim 1 wherein the supercritical fluid is a mixture of carbon dioxide and chloroform.
8. A process for extracting a compound from plant material, comprising contacting the plant material with an acid, a supercritical fluid and a co-solvent, and recovering the compound from the supercritical fluid.
9. The process of claim 8 wherein the compound being extracted is a sterol compound or a fatty acid.
10. The process of claim 8 wherein the plant material is hydrolyzed with a mineral or organic acid.
11. The process of claim 10 wherein the mineral acid is sulfuric or hydrochloric acid.
12. The process of claim 10 wherein the organic acid is paratoluene sulfonic acid.
13. The process of claim 8 wherein the supercritical fluid is carbon dioxide.
14. The process of claim 10 wherein the supercritical fluid is carbon dioxide and the co-solvent is carbon tetrachloride.
15. The process of claim 8 wherein the co-solvent is isopropyl alcohol.

16. A process for extracting a compound from plant material which is Barbasco root or Yucca seed, comprising contacting the Barbasco root or Yucca seed with an acid, a supercritical fluid and a co-solvent, and recovering the compound from the supercritical fluid.

17. A process for extracting diosgenin or sarsapogenin from plant material, comprising contacting the plant material with an acid, a supercritical fluid and a co-solvent, and recovering the diosgenin or sarsapogenin from the supercritical fluid.

18. A process for extracting diosgenin or sarsapogenin from plant material comprising
   a) contacting acid-hydrolyzed plant material with a supercritical fluid, optionally with a co-solvent, and
   b) recovering the diosgenin or sarsapogenin from the supercritical fluid.

19. A process for extracting a compound from plant material which is Barbasco root or Yucca seed comprising
   a) contacting acid-hydrolyzed plant material with a supercritical fluid, optionally with a co-solvent, and
   b) recovering the compound from the supercritical fluid.

* * * * *